United States Patent
Citek et al.

(10) Patent No.: US 9,404,863 B2
(45) Date of Patent: *Aug. 2, 2016

(54) EYEGLASS RATING WITH RESPECT TO PROTECTION AGAINST UV HAZARD

(71) Applicant: ESSILOR INTERNATIONAL (COMPAGNIE GENERALE D'OPTIQUE), Charenton le Pont (FR)

(72) Inventors: Karl Citek, Forest Grove, OR (US); Gilles Baillet, Charenton-le-Pont (FR); Francisco De Ayguavives, Charenton-le-Pont (FR); Gabriel Keita, Dallas, TX (US)

(73) Assignee: ESSILOR INTERNATIONAL (COMPAGNIE GENERALE D'OPTIQUE), Charenton le Pont (FR)

( * ) Notice: Subject to any disclaimer, the term of this patent is extended or adjusted under 35 U.S.C. 154(b) by 76 days.

This patent is subject to a terminal disclaimer.

(21) Appl. No.: 14/003,159

(22) PCT Filed: Dec. 13, 2012

(86) PCT No.: PCT/EP2012/075406
§ 371 (c)(1),
(2) Date: Sep. 4, 2013

(87) PCT Pub. No.: WO2013/092377
PCT Pub. Date: Jun. 27, 2013

(65) Prior Publication Data
US 2013/0341523 A1    Dec. 26, 2013

(30) Foreign Application Priority Data
Dec. 23, 2011 (EP) .................................... 11306764

(51) Int. Cl.
*G01N 21/59* (2006.01)
*B07C 5/342* (2006.01)
(Continued)

(52) U.S. Cl.
CPC ................ *G01N 21/59* (2013.01); *B07C 5/342* (2013.01); *G01J 1/429* (2013.01);
(Continued)

(58) Field of Classification Search
CPC ....... G01N 21/33; G01N 21/55; G01N 21/59; G01N 2021/558; G01N 2021/0616; A61F 9/02; B07C 5/342
See application file for complete search history.

(56) References Cited

U.S. PATENT DOCUMENTS 4,549,081 A    10/1985   Ace
5,949,535 A     9/1999   Hall
(Continued)

OTHER PUBLICATIONS

"Sunscreen", WIkipedia, accessed Oct. 29, 2013 <en.wikipedia.org/wiki/sunscreen#/Sun_protection_factor_.28SPF.29_and_labeling_requirements>.*

(Continued)

*Primary Examiner* — Casey Bryant
(74) *Attorney, Agent, or Firm* — Oblon, McClelland, Maier & Neustadt, L.L.P.

(57) ABSTRACT

An index value is calculated for rating an eyeglass with respect to protection against UV hazard. The index value is based on an integrated UV transmission value through the eyeglass and an integrated UV reflection value related to a back face of the eyeglass. Thus, the index value takes into account actual wearing conditions where UV eye exposure is due either to transmission through the eyeglass or reflection on the eyeglass back face. Respective index values obtained for a set of eyeglasses allow easy sorting of the eyeglasses with respect to UV protection efficiency.

17 Claims, 3 Drawing Sheets

(51) Int. Cl.
*G01M 11/02* (2006.01)
*G01N 21/33* (2006.01)
*G02C 7/10* (2006.01)
*G01J 1/42* (2006.01)
*G02C 7/02* (2006.01)
*A61F 9/02* (2006.01)
*G01N 21/55* (2014.01)

(52) U.S. Cl.
CPC .......... *G01M 11/0285* (2013.01); *G01N 21/33* (2013.01); *G02C 7/028* (2013.01); *G02C 7/10* (2013.01); *A61F 9/02* (2013.01); *G01N 21/55* (2013.01); *G01N 2021/558* (2013.01); *G01N 2201/0616* (2013.01)

(56) References Cited

U.S. PATENT DOCUMENTS

2003/0095256 A1   5/2003   Cargill et al.
2010/0007873 A1   1/2010   Cado
2012/0200847 A1   8/2012   Hall

OTHER PUBLICATIONS

International Search Report issued Jan. 30, 2013 in Application No. PCT/EP2012/075406.
Karl Citek, "Anti-reflective coatings reflect ultraviolet radiation", Optometry, vol. 79, No. 3, 2008, pp. 143-148.
Karl Citek, "The Eye and Solar Ultraviolet Radiation", Roundtable-UV 201, Moderator: Karl Citek, URL http://www.espf.com/wp-content/uploads/2012/04/The-eye-and-solar-ultraviolet-radiation-Karl-Citek-roundtable-UV-2011-Karl-Citek.pdf, Jun. 18, 2011, pp. 1-19.
"Ophthalmic optics-Spectacle lenses-Vocabulary", International Standard, ISO 13666, XP009159547, 1998, 64 pages.
Essilor International, "The Eye-Sun Protection Factor (E-SPF): A New Way to Look at Ultraviolet Radiation Hazard and Eye Protection", RCS Creteil B 712 049618, XP 002676423, Jan. 1, 2012, 1 page.
Essilor International, "Maximizing Protection from Ultraviolet Radiation, Hazards: Assessing the Risks; Finding Solutions", Crizal Technical Paper, XP002676425, 2012, pp. 1-4.
Gary W. Hall, et al., "The FUBI system for solar rating nonprescription eyewear", Optometry—Journal of the American Optometric Association, vol. 73, No. 7, XP009159631, Jul. 2002, pp. 407-417.

\* cited by examiner

$$\tau_{UV} = \frac{\int_{UVA \& UVB} Es(\lambda) \times S(\lambda) \times \tau(\lambda) \times d\lambda}{\int_{UVA \& UVB} Es(\lambda) \times S(\lambda) \times d\lambda}$$

FIG. 2b

$$R_{UV} = \frac{\int_{UVA \& UVB} Es(\lambda) \times S(\lambda) \times R(\lambda) \times d\lambda}{\int_{UVA \& UVB} Es(\lambda) \times S(\lambda) \times d\lambda}$$

FIG. 3a

$$E\text{-}SPF = \frac{BN}{\alpha \times R_{UV}(i_R) + \beta \times \tau_{UV}(i_T) + \gamma}$$

FIG. 3b

$$E\text{-}SPF = \frac{1}{R_{UV}(145°) + \tau_{UV}(0°)}$$

| Wavelength  Longueur d'onde  Wallenlänge  nm | Solar spectral irradiance  Irradiation solaire spectrale  Solare Bestrahlungsstärke  $E_S\lambda$ mW/m$^2$/nm | Relative spectral effectiveness function  Fonction d'efficacité relative spectrale  Relative spektrale Wirksamkeitsfunktion  S | Weighting function  Fonction de pondération  Bewertungsfunktion  $W=E_S\lambda \cdot S$ |
|---|---|---|---|
| 280 | 0 | 0,88 | 0 |
| 285 | 0 | 0,77 | 0 |
| 290 | 0 | 0,64 | 0 |
| 295 | 2,09 x 10$^{-1}$ | 0,54 | 0,000 11 |
| 300 | 8,10 x 10$^{-2}$ | 0,30 | 0,024 3 |
| 305 | 1,91 | 0,060 | 0,115 |
| 310 | 11,0 | 0,015 | 0,165 |
| 315 | 30,0 | 0,003 | 0,090 |
| 320 | 54,0 | 0,001 0 | 0,054 |
| 325 | 79,2 | 0,000 50 | 0,040 |
| 330 | 101 | 0,000 41 | 0,041 |
| 335 | 128 | 0,000 34 | 0,044 |
| 340 | 151 | 0,000 28 | 0,042 |
| 345 | 170 | 0,000 24 | 0,041 |
| 350 | 188 | 0,000 20 | 0,038 |
| 355 | 210 | 0,000 16 | 0,034 |
| 360 | 233 | 0,000 13 | 0,030 |
| 365 | 253 | 0,000 11 | 0,028 |
| 370 | 279 | 0,000 093 | 0,026 |
| 375 | 306 | 0,000 077 | 0,024 |
| 380 | 336 | 0,000 064 | 0,022 |

FIG. 2c

EYEGLASS RATING WITH RESPECT TO PROTECTION AGAINST UV HAZARD

The invention relates to a method of rating an eyeglass and also a method of sorting a set of eyeglasses, with respect to protection against UV hazard.

BACKGROUND OF THE INVENTION

Hazards due to UV radiation for human eyes have been suspected and studied for long time. For example, document U.S. Pat. No. 5,949,535 contains a presentation of some of the damages which may be caused by UV radiation upon the eye. In everyday life, most of the UV radiation encountered originates from the Sun, although some of the existing artificial light sources also produce significant amounts of UV radiation.

It is also known that eyewear can provide protection against UV hazard to a wearer. For example, the already-mentioned document U.S. Pat. No. 5,949,535 discloses rating an eyewear according to its solar radiation protection capabilities, in particular in the UV range. Then a user of the eyewear can be informed about its protection efficiency against UV hazard by providing him with a numeral value which quantifies this protection efficiency. The rating method disclosed in this prior art document is based on at least two of the following values: a first transmission value for each eyeglass in the UV wavelength range from 280 nm (nanometer) to 400 nm, a second transmission value for each eyeglass in the blue wavelength range from 400 nm to 500 nm, and a further value for quantifying the amount of incident light that reaches the eye from around the frame which holds the eyeglass on the wearer's face. More precisely, this latter value represents the extraneous light that reaches the eye without being filtered through the eyeglass or absorbed or reflected by the eyewear frame.

But this known rating method does not quantify appropriately in all circumstances the total UV radiation amount which enters into the eye of the eyewear wearer. In particular, there exists some conditions where significant amount of radiation enters into the eye but without being taken into account by this method.

Therefore, an object of the present invention is to provide rating of an eyeglass that quantifies more significantly the protection against UV hazard which is produced by the eyeglass. In particular, the rating should take into account most of the actual conditions of UV eye exposure which occur actually.

Another object of the present invention is to provide a value for rating an eyeglass with respect to UV protection, which can be understood easily and directly by a customer intending to acquire the eyeglass.

Still another object of the invention is to provide a rating value for an eyeglass with respect to UV protection, which can be determined easily, in particular by measuring and/or calculating appropriate optical values.

SUMMARY OF THE INVENTION

For meeting these objects and others, a first aspect of the invention proposes a method of rating an eyeglass with respect to protection which is provided by this eyeglass against UV hazard, whereby an index value is calculated for quantifying a reduction in a total UV amount that impinges onto an eye for a wearer of the eyeglass with respect to UV exposure without eyeglass, the method comprising the following steps:

/1/ providing a value of UV transmission for the eyeglass, obtained by integrating spectral transmission values weighted for quantifying hazard and intensity for each wavelength value, over a determined UV wavelength range;

/2/ providing a value of UV reflection on a back face of the eyeglass, the UV reflection being obtained by integrating spectral reflection values relating to the back face of the eyeglass, and weighted for quantifying the hazard and intensity for each wavelength value, over the determined UV wavelength range;

/3/ combining both values of UV transmission and UV reflection of the eyeglass using an addition formula with non-zero positive factors respectively for the UV transmission and UV reflection; and /4/ calculating the index value from a base number divided by a result obtained in step /3/.

Thus, the rating method of the invention is efficient for taking into account varying eye exposure conditions to UV radiation. First ones of these conditions occur when the wearer's face is oriented towards the UV source. Then, the transmission of UV radiation through the eyeglass is the main exposure mode of the wearer's eye to UV radiation, and this contribution participates to the index value through the UV transmission value of the eyeglass involved in the addition formula.

But second exposure conditions also occur when the wearer's face is oriented away from the UV source, for example with an angle of between 135° and 160° between the direction of the UV source and the forward direction of the wearer's face. In such conditions, no UV radiation is transmitted through the eyeglass to the eye, but some radiation impinges onto the back face of the eyeglass from the UV source around the wearer's head, mainly on both external lateral sides, and is reflected by the eyeglass to the eye. This other exposure mode is separate from that which involves transmission through the eyeglass, but also participates to the UV eye exposure when the wearer is equipped with the eyeglass. According to the invention, this reflection-based exposure mode also participates to the index value, through the UV reflection value which is also involved in the addition formula.

Hence, the rating method of the invention is efficient for taking into account UV eye exposure conditions due to radiation transmission through the eyeglass but also radiation reflection by the back face of the eyeglass.

Optionally, the index value may be obtained in step /4/ from the ratio of the base number to the result for the addition formula filled in with the UV transmission and UV reflection values of the eyeglass, by further implementing an offset or correcting term. Such offset or correcting term may be added to the ratio of the base number to the result of the addition formula. It may depend on geometric parameters such as position of the UV source with respect to the eyeglass, spectacle frame parameters, physionomic parameters of the wearer, lens sizing and curvature parameters, etc.

Preferably, the index value calculated in step /4/ may be equal to the base number divided by the result obtained in step /3/ for the combining of the UV transmission and UV reflection values of the eyeglass using the addition formula.

In preferred implementations of the invention, the result of the addition formula may be unity when replacing in this formula the UV transmission of the eyeglass with a maximum value due to a scale used for the UV transmission, and also replacing the UV reflection of the eyeglass with zero. Then, the result of the addition formula when using the UV transmission and the UV reflection values of the eyeglass may equal a reduction factor for the total UV eye exposure when the wearer is equipped with the eyeglass, as compared with the wearer without eyeglass. Put another way, the result of the addition formula quantifies the efficiency of the eyeglass for protecting the eye against UV hazard in everyday life. Such meaning of the index value provided by the invention is easy and simple to understand.

The invention may be used for rating an eyeglass with respect to hazard related to any UV source, natural or artificial, provided that the weighting function used in steps /1/ and /2/ corresponds to this UV source. This comprises that the weighting function for the spectral transmission and reflection values of the eyeglass is based on spectral irradiance values which correspond to the actual UV source. When the Sun is the UV source considered, the quantifying of intensity for each wavelength value in steps /1/ and /2/ may be implemented by using values of solar spectral irradiance as a factor within a weighting function for the spectral transmission and spectral reflection values of the eyeglass.

Preferably, the addition formula used in step /3/ may be $\alpha \cdot R_{UV} + \beta \cdot \tau_{UV} + \gamma$, where $\tau_{UV}$ and $R_{UV}$ are respectively the UV transmission and the UV reflection of the eyeglass, $\alpha$ and $\beta$ are the factors respectively for the UV reflection and the UV transmission of the eyeglass, and $\gamma$ is a constant value. The constant value $\gamma$ may be non-zero. Then, it may stand for a UV intensity amount which includes solar UV radiation diffused before entering into a wearer's eye. This UV intensity amount may also include direct solar UV radiation with incidence direction such that this radiation enters into the wearer's eye after passing outside a peripheral edge of a frame used with the eyeglass when the wearer is equipped with the eyeglass. In both cases, the constant value $\gamma$ may be obtained from measurements performed with reference conditions in day time, of the UV intensity amount including the solar UV radiation diffused before entering into the wearer's eye, and possibly also including the direct solar UV radiation which enters into the wearer's eye from around the eyeglass.

In alternative preferred implementations of the invention, the factors for the UV reflection and the UV transmission values of the eyeglass in the addition formula may be both equal to unity, and the constant value may be zero. Very simple calculations then lead to the index value for any eyeglass.

The determined UV wavelength range which is used in both steps /1/ and /2/ may be either a first range from 280 nm to 380 nm, or a second range from 280 nm to 400 nm, or a third range from 315 nm to 380 nm, or a fourth range from 280 nm to 315 nm.

A second aspect of the invention proposes a method of sorting a set of eyeglasses with respect to protection provided by each of these eyeglasses against UV hazard, which method comprises the following steps:

for each one of the eyeglasses, calculating a respective index value by implementing a rating method as described above; and comparing with each other the index values obtained respectively for the eyeglasses.

Thus, a customer who intends to acquire one of the eyeglasses can select it based on clear information about their respective protection efficiencies against UV hazard. He can sort the eyeglasses with respect to their index values while being aware of an absolute protection efficiency of each eyeglass compared to bare-eye conditions.

The invention is described now in detail for non-limiting implementations, with reference to the figures now listed.

BRIEF DESCRIPTION OF THE DRAWINGS

Figure 1:
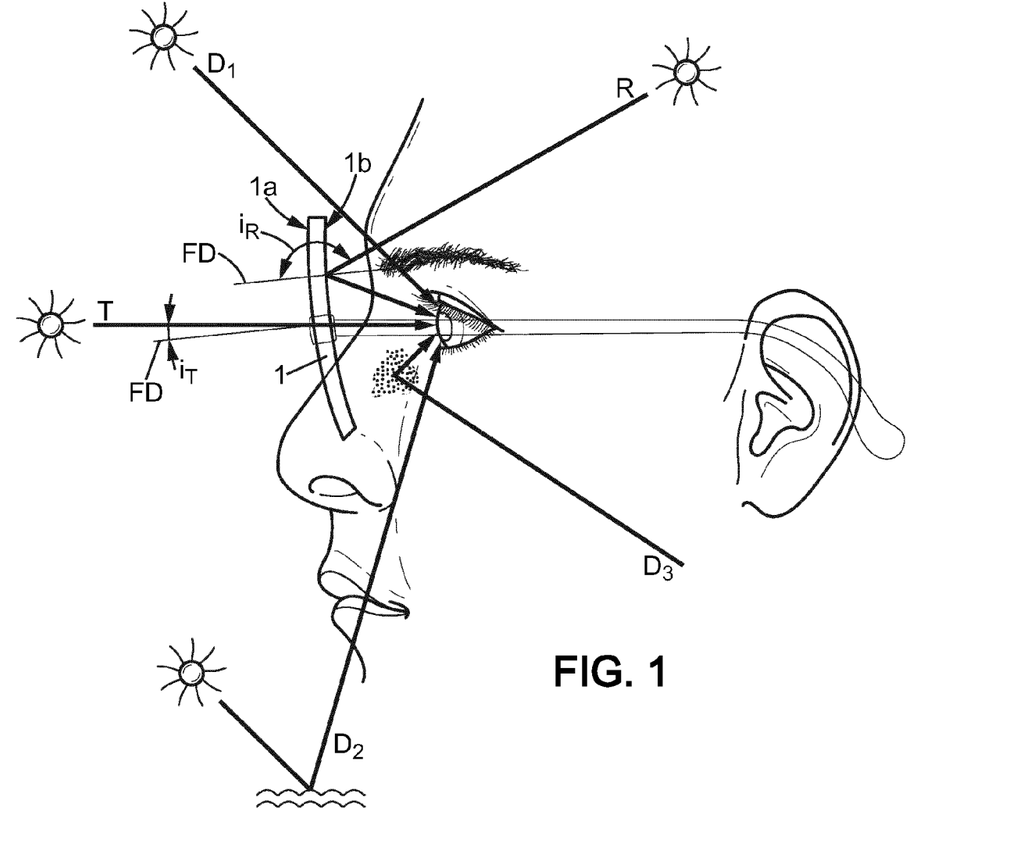
FIG. 1 illustrates radiation streams impinging onto an eye of an eyeglass wearer.

For sake of clarity, the elements represented in FIG. 1 are not sized in relation with actual dimensions, nor with ratios of actual dimensions. In addition, same characters used in different figures have identical meaning.

DETAILED DESCRIPTION OF THE INVENTION

The UV part of the solar radiation which is transmitted through the Earth atmosphere is usually divided into two wavelength ranges: UV A corresponding to wavelength values from 380 nm (nanometer) at the boundary with the visible range down to 315 nm, and UV B for wavelength values from 315 nm down to 280 nm. UV radiation originating from the Sun with wavelength below 280 nm, denoted UV C, is absorbed by the ozone of the atmosphere, so that anyone is not exposed to UV C in everyday life, unless exceptional conditions which are not encountered by most of people. In addition, radiation with wavelength comprised between 380 nm and 400 nm may also be considered as pertaining to the UV range. However, in the detailed description below and unless indicated differently, the UV wavelength range considered for solar radiation may extend from 280 nm to 380 nm, although the invention may be applied to other UV ranges.

In a known manner, UV A radiation is absorbed by the eye crystalline lens of a human being, and the most important part of the UV B radiation is absorbed by the cornea. Known ocular pathologies are related to these UV radiations, so that protection of the eye against UV exposure is an issue with growing interest. In particular, UV B radiation is known to be more dangerous than UV A radiation. The present invention aims at quantifying such protection for eyeglasses such as spectacle eyeglasses, in a simple to calculate and understand but meaningful way.

It applies to any spectacle eyeglass: ametropia-correcting eyeglass, progressive addition eyeglass, multifocal eyeglass, plano eyeglass, solar glass, etc, whatever the base material of the eyeglass: mineral, organic or hybrid. It also applies to eyeglasses which are provided with one or more coatings or layers on at least one of their optical faces, namely their front face, back face, both front and back faces, and/or possibly on an additional interface of the eyeglass located between the front face and the back face. In particular, it applies to eyeglasses which are provided with anti-reflecting coatings on their back face, as it will be indicated later on that such reflection is important in some circumstances.

The invention also applies to eyeglasses for goggles, whatever is the curvature of the eyeglass, the exact form of the frame, in particular the lateral parts of the frame, the material of the frame, etc. In particular, the invention is compatible with configurations where a single elongated eyeglass extends continuously in front both eyes of the wearer. It is also compatible with lateral parts of the frame which are UV transmitting or UV blocking.

FIG. 1 shows schematically several radiation flows which impinge onto the eye of the eyeglass wearer. Reference numbers 1, 1a and 1b denote respectively the eyeglass, its front face and its back face. The radiation flows are now listed:

- T: the radiation originating directly from the Sun and transmitted through the eyeglass 1, from the front face 1a to the back face 1b, and then reaching the eye;
- R: the radiation originating directly from the Sun and reflected on the back face 1b of the eyeglass 1, and then reaching the eye;
- $D_1$: the radiation originating directly from the Sun, passing around the eyeglass 1 outside the peripheral edge of this latter and a frame used with the eyeglass 1, and reaching the eye;
- $D_2$: the radiation originating indirectly from the Sun, because of being diffused by elements contained in the wearer's environment such as ground or water surface before passing around the eyeglass 1 and reaching the eye; and
- $D_3$: the radiation originating indirectly from the Sun, because of being diffused by the wearer's skin or the eyeglass frame before reaching the eye.

These radiation flows apply in particular for UV radiation.

The radiation flows T and R depend on the eyeglass features, in particular on its values of transmission and reflection respectively. But they may also depend on further eyeglass features such as the eyeglass dimensions, the base value, the prism value, the pantoscopic angle value, etc. As well-known in ophthalmics, the base value of an eyeglass relates to its curvature value at a reference point in its front face. Because of the originating directions of the radiation flows T and R with respect to the eyeglass 1, these flows T and R do not exist simultaneously. Indeed, the radiation flow T is non-zero when the wearer's face is oriented towards Sun side, and then direct solar radiation cannot reach the back face 1b of the eyeglass 1. Conversely, the radiation flow R is non-zero when the wearer's face is oriented away from Sun side, and then direct solar radiation cannot reach the front face 1a of the eyeglass 1 for passing through this latter. But radiation flows T and R may occur after one another when the eyeglass wearer is turning from facing initially South direction until facing North side with about 30° offset from the North direction.

In addition, the radiation flow T impinges on the front face 1a of the eyeglass 1 with a value for the incidence angle $i_T$ which depends on the azimuth-orientation of the wearer's head, but also the time within the day period and the latitude at the surface of the Earth for the Sun height, the pantoscopic angle, etc. However, because transmission usually changes only with limited extent as long as the incidence angle $i_T$ is not too large, one may consider that the value for the transmission through the eyeglass 1 at 0° (degree) for the incidence angle $i_T$ nearly always applies. The incidence angle is measured with respect a reference direction FD which oriented forwards for the eyeglass 1, i.e. ahead from the front face 1a.

The value of the incidence angle $i_R$ for the radiation flow R on the eyeglass back face 1b needs to allow for the flow R to propagate between the edge of the eyeglass 1 and the wearer's head. Because of that, the value of the incidence angle $i_R$ of the radiation flow R, again with respect to the reference direction FD, is between 135° and 160°, more often between 145° and 150°. Such angle values do not appear actually in FIG. 1, because the propagation direction of the radiation flow R is not contained within the sectional plane of this figure. It is repeated again that direct solar radiation is not transmitted through the eyeglass 1 with $i_T$-angle and reflected with $i_R$-angle at the same time.

Radiation flows $D_1$ to $D_3$ do not depend of the eyeglass transmission and reflection values, but they may depend on other parameters such as the eyeglass dimensions, geometrical features of the frame and the wearer's face, etc. In addition, energy spectral distributions of the radiation flows $D_2$ and $D_3$ do not depend only on the solar irradiance, because these flows are diffused before reaching the eye. For this reason, the spectral diffusion efficiency of the diffusing elements may play a significant role. By way of simplicity, the respective radiation energies of the flows $D_1$ to $D_3$ at the eye surface may be summed within a resulting radiation contribution D, so that $D=D_1+D_2+D_3$. For some circumstances where the total energy value of the radiation contribution D is much less than the energy amount of the radiation flow T or R, or for sake of simplicity in the index value calculation, one may consider that radiation contribution D equals zero.

International Standard ISO 13666 indicates a manner for calculating a transmission in the solar UV A spectrum, as well as a transmission in the solar UV B spectrum. Both are expressed as continuous sums, i.e. integration, over the corresponding UV A and UV B wavelength ranges, of the spectral transmission of the eyeglass weighted with the solar spectral irradiance $Es(\lambda)$ multiplied by a relative spectral effectiveness function $S(\lambda)$ for UV radiation. The product of $Es(\lambda)$ with $S(\lambda)$ then appears as the actual weighting function of the spectral transmission, and is denoted $W(\lambda)$. In the context of the present description, transmission and transmittance are used equivalently, provided that the Man skilled in optics knows that they are inter-related by a reference area factor.

Figure 2A:
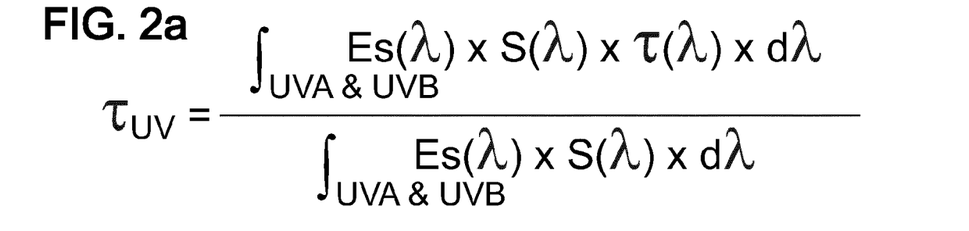
FIGS. 2a and 2b reproduce mathematical expressions for calculating UV transmission and UV reflection values for an eyeglass.

FIG. 2a contains an expression for the transmission of the eyeglass in the UV total solar spectrum, corresponding to UV A and UV B spectra joined together. This expression is consistent with those of the Standard ISO 13666 for the UV A and UV B ranges separately. In accordance with the indications reported above, the total solar spectrum UV A & UV B may correspond to the wavelength range extending from 280 nm to 380 nm. $\tau(\lambda)$ denotes the spectral transmission through the eyeglass, and $\tau_{UV}$ is the UV transmission of the eyeglass, also called mean UV solar transmission of the eyeglass.

Figure 2B:
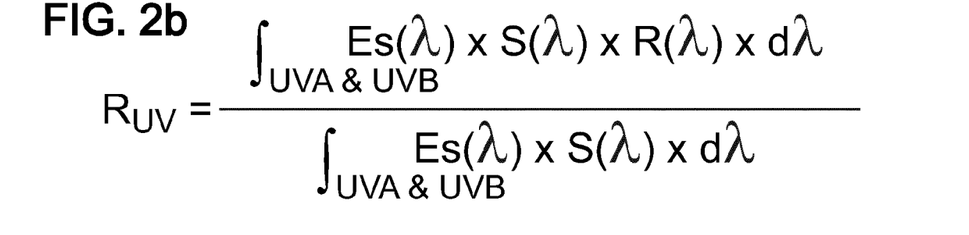

FIG. 2b corresponds to FIG. 2a for the UV radiation reflection on the back face of the eyeglass. $R(\lambda)$ denotes the spectral reflection on the eyeglass back face, and $R_{UV}$ is the UV reflection on the eyeglass back face, also called mean UV solar reflection of the eyeglass.

Figure 2C:
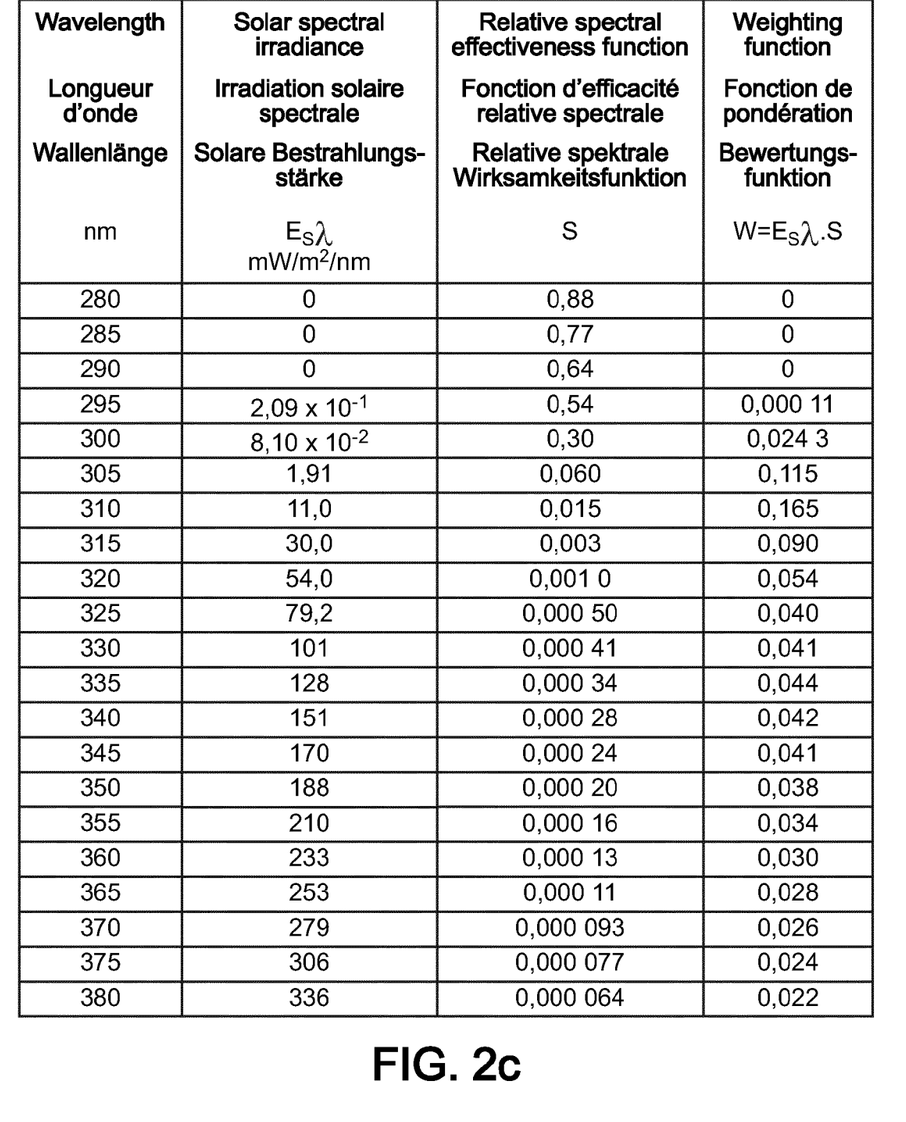
FIG. 2c is a table containing spectral weighting values which may be used in implementations of the invention.

In both expressions of the UV transmission and UV reflection of FIGS. 2a and 2b, the continuous sums over the UV wavelength range may be replaced with discrete sums, for example using a wavelength pitch of 5 nm. Other wavelength pitch values may be used alternatively, provided that the values of the solar spectral irradiance $Es(\lambda)$ and the relative spectral effectiveness function $S(\lambda)$ are interpolated appropriately. Annex A of Standard ISO 13666 contains a table which is reproduced in FIG. 2c, with the values of the solar spectral irradiance $Es(\lambda)$ and the relative spectral effectiveness function $S(\lambda)$ for each UV wavelength $\lambda$ with a 5 nm pitch, from 280 nm to 380 nm. This table can thus be used for calculating the UV transmission and UV reflection values.

Figure 3A:
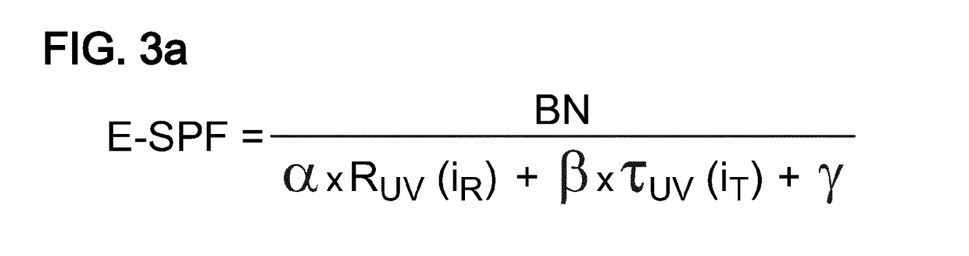
FIGS. 3a and 3b reproduce possible mathematical expressions suitable for calculating an index value according to the invention.

FIG. 3a displays a possible mathematical formula for the index value of the invention. This index is denoted E-SPF® standing for eye-solar protection factor. In this formula:
- BN is a base number which is constant and non-zero, and acts as a scale factor for the index;
- $\tau_{UV}(i_T)$ is the UV transmission of the eyeglass as described above, assessed for the incidence angle value $i_T$;
- $R_{UV}(i_R)$ is the UV reflection of the eyeglass back face as described above, assessed for the incidence angle value $i_R$;
- α and β are the factors respectively of the UV reflection $R_{UV}$ and the UV transmission $\tau_{UV}$; and
- γ is a constant value.

For consistency with the geometrical considerations reported with reference to FIG. 1, the UV transmission $\tau_{UV}$ may be provided for a first value of the incidence angle $i_T$ of UV rays onto the eyeglass 1, which is less than 30°. The UV reflection $R_{UV}$ may be provided for a second value of the incidence angle $i_R$ of the UV rays onto the back face 1b of the eyeglass 1, which is between 135° and 160°, with both incidence angles $i_T$ and $i_R$ measured from the forward-oriented reference direction FD of the eyeglass.

Using non-zero values for both factors α and β enables that the index value obtained is meaningful for conditions where the UV eye exposure is due to radiation transmission through the eyeglass, but also when the UV eye exposure is due to radiation reflection on the back face of the eyeglass. This is especially advantageous since UV eye exposure by back-face reflection may form the most important contribution to the total exposure over a long time-period in some cases, for example with sunglasses with large open gaps between the lateral eyeglass edges and the wearer's temples, and for conditions where the solar height is low.

Preferably, the ratio of the factor β to the base number BN, i.e. β/BN, may be in the range from 0.01 to 1. Similarly, the ratio α/BN may also be in the same range from 0.01 to 1. More preferably, a/BN is equal to or higher than, 0.2, 0.4, 0.5 or 0.6 in the order of increasing preference, while remaining less than or equal to 1. In parallel, β/BN is equal to or higher than, 0.4, 0.5, 0.6 or 0.7 also in the order of increasing preference, again while remaining less than or equal to 1. A preferred combination is a/BN and β/BN both in the range from 0.5 to 1.

Generally, factors α and β stands in particular for the role of geometrical factors relating to the eyeglass or eyeglass wearing conditions, such as the eyeglass area for factor β, and the area of the open gap between the eyeglass and the wearer's temple for factor α. Both factors β and α may be obtained from photometric measurements performed respectively for direct solar UV intensity impinging onto a wearer's eye and direct solar UV intensity impinging onto the back face of the eyeglass from back side of the wearer's head, respectively corresponding to the radiation flows T and R. For such measurements, reference values may be used for parameters which are selected among illumination parameters in day time, sizing and wearing parameters of a spectacle frame used with the eyeglass, and the base parameter of the eyeglass. In some implementations of such measurements, the factors α and β may be obtained from averaged measurement results which are performed with varying some of the illumination parameters selected among solar time, azimuth direction of the wearer's head, inclination of the wearer's head, season, date within the year, latitude on the Earth, etc.

The constant value γ stands for the total radiation contribution D. It may be zero for simplified implementations of the invention, or may be non-zero with value obtained from measurements performed with reference conditions in day time, of a UV intensity amount including the solar UV radiation flows $D_2$ and $D_3$ which are diffused before reaching the wearer's eye. In this case, the UV intensity amount which is measured for obtaining the constant value γ, may further include the direct solar UV radiation flow $D_1$ with incidence direction such that this radiation flow reaches the wearer's eye after passing outside the peripheral edge of the frame used with the eyeglass when the wearer is equipped so.

The factors α and β and the constant value γ may be determined by irradiance measurements using a sensor placed at the eye location on the head of a dummy model simulating the wearer. The measurements are conducted in a solar environment, while the eyeglass is mounted in spectacles on the model's head in the same position as if it were worn actually by the wearer.

In a first experiment, the back face of the eyeglass is covered by a UV-blocking material, for example an opaque material absorbing all visible and UV rays impinging onto the front face of the eyeglass and transmitted to its back face, as well as UV rays impinging onto the back face. Thus no UV ray reaches the sensor, which would originate from forwards through the eyeglass and from backwards with reflection onto the eyeglass back face. The γ constant value can then be determined.

In a second experiment, the UV-blocking material is covered onto the front face of the eyeglass. The sensor measures then, in addition to γ constant value, the irradiance part due to the reflection on the back face of the eyeglass. The value of the factor α can thus be calculated.

In a third and last experiment, the whole irradiance received by the eye of the wearer is measured by the sensor, and the value of the factor β can also be obtained.

Figure 3B:
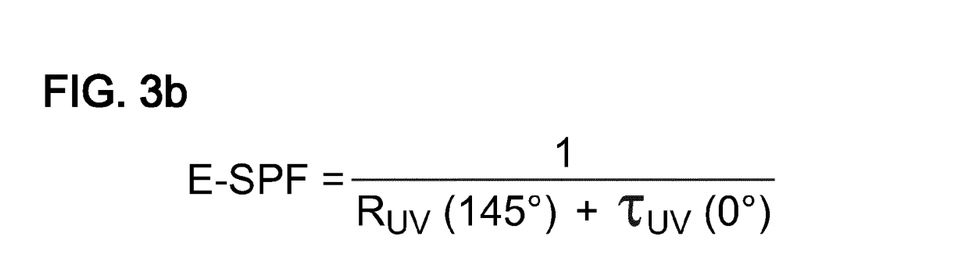

FIG. 3b corresponds to FIG. 3a for a preferred implementation of the invention. In this implementation, the factors α and β of both the UV reflection $R_{UV}$ and the UV transmission $\tau_{UV}$ are equal to unity, and the constant value is zero: α=β=1 and γ=0. The base number BN may be equal to unity too.

For example, the E-SPF value thus calculated may be based on a value for the UV reflection which is assessed for the incidence angle $i_R$ of 145°, and a value for the UV transmission which is assessed for the incidence angle $i_T$ of 0°. Such E-SPF value is easy to calculate for any eyeglass, from UV transmission and UV reflection values obtained in accordance with the formulae of FIGS. 2a and 2b.

The expression of FIG. 3b for the E-SPF index has been used for rating four eyeglasses obtained by combining two base eyeglasses with two anti-reflecting coatings arranged on the back faces of the base eyeglasses. The first base eyeglass, denoted base eyeglass 1, has a UV transmission $\tau_{UV}(0°)$ at zero value for the incidence angle $i_T$ which is equal to about 5%, and the UV transmission $\tau_{UV}(0°)$ of the second base eyeglass, denoted base eyeglass 2, is zero. The first coating, denoted coating 1, is efficient mainly in the visible wavelength range, whereas the second coating, denoted coating 2, has been optimized for minimizing back face reflection in the UV range at about 145° for the incidence angle $i_R$. Thus, for both base eyeglasses 1 and 2, the UV reflection $R_{UV}(145°)$ of coating 1 equals around 13%, and that of coating 2 equals around 4%. The table here-below gathers the E-SPF values which are obtained for the four eyeglasses:

|  | Base eyeglass 1 $\tau_{UV}(0°) = 5\%$ | Base eyeglass 2 $\tau_{UV}(0°) = 0\%$ |
|---|---|---|
| Coating 1 $R_{UV}(0°) = 13\%$ | Eyeglass 1 E-SPF = 6 | Eyeglass 2 E-SPF = 8 |
| Coating 2 $R_{UV}(0°) = 4\%$ | Eyeglass 3 E-SPF = 11 | Eyeglass 4 E-SPF = 25 |

Thus, the invention enables to sort easily and efficiently the eyeglasses with respect to the eye protection which is provided by each of them against UV hazard. First, the respective index value is calculated for each one of the eyeglasses. Then, the index values which have been obtained respectively for the eyeglasses are compared with each other.

Generally for the present invention, the result of the addition formula at the denominator of the index value, namely $\alpha \cdot R_{UV} + \beta \cdot \tau_{UV} + \gamma$, may be obtained directly from measurements performed with the eyeglass using a bench photometer designed for simulating outside illumination conditions in day time. To this purpose, UV sources possibly with filters selected so as to reproduce the weight function $W(\lambda)$ may be located in front of the eyeglass 1, and behind it with angular offset equal to $180°-i_R$, and optionally additional UV sources for reproducing the radiation flows $D_1$ to $D_3$. All UV sources are activated simultaneously, and a UV photometer located behind the eyeglass captures the total UV radiation amount at the location of the wearer's eye with respect to the eyeglass.

The invention may be implemented while adapting or modifying some details with respect to the specification just above, but maintaining at least some of its advantages. In particular, the numeral values cited are only for illustrative purpose, and may be adapted.

Additionally, alternative implementations of the invention may be obtained by modifying the wavelength range of the UV radiations, which is used for calculating both values of the UV transmission $\tau_{UV}$ and the UV reflection $R_{UV}$. Then, the index value E-SPF is obtained for the UV wavelength range selected, based on the values of the UV transmission $\tau_{UV}$ and UV reflection $R_{UV}$ which have been calculated for this selected UV wavelength range. The modified UV wavelength range is thus to be taken into account in the formulae of FIGS. 2a and 2b in place of UVA & UVB ranging as a whole from 280 nm to 380 nm, and the resulting modified results for the UV transmission $\tau_{UV}$ and UV reflection $R_{UV}$ will propagate into the formulae of FIGS. 3a and 3b.

In first ones of these alternative implementations, the UV wavelength range from 280 nm to 380 nm as used before in the detailed description may be replaced with the extended UV wavelength range from 280 nm to 400 nm.

In second ones of the alternative implementations, the UV wavelength range may be limited to the UV A radiations, from 315 nm to 380 nm. Then, the formulae of FIGS. 2a and 2b lead to values for a UV A transmission value, namely $\tau_{UV\,A}$, and a UV A reflection value, $R_{UV\,A}$. A value for the index E-SPF is then obtained which relates to the UV A radiations only: E-SPF(UV A).

Third alternative implementations are obtained in a similar manner by using the UV B wavelength range only: from 280 nm to 315 nm, instead of the UV A wavelength range of the second implementations. Thus, a UV B transmission value $\tau_{UVB}$, a UV B reflection value $R_{UVB}$ and a value for the index E-SPF(UV B) are obtained, which relate to the UV B radiations.

However, one should pay attention about the following inequalities:

$\tau_{UVA}+\tau_{UVB}\neq\tau_{UV}$ as this latter $\tau_{UV}$ is shown in FIG. 2a using the merging of the UV A and UV B ranges, $R_{UV\,A}+R_{UV\,B}\neq R_{UV}$ as the latter $R_{UV}$ is shown in FIG. 2b using the merging of the UV A and UV B ranges, and E-SPF(UV A)+E-SPF(UV B)≠E-SPF as this latter E-SPF value results from the formula of FIG. 3a or 3b where the values of $\tau_{UV}$ and $R_{UV}$ are obtained for the merging of the UV A and UV B ranges.

The invention claimed is:

1. A method of rating an eyeglass with respect to protection provided by the eyeglass against UV hazard, whereby an index value is calculated for quantifying a reduction in a total UV amount impinging onto an eye for a wearer of the eyeglass with respect to UV exposure without eyeglass, the method comprising:

obtaining a measurement of UV intensity, the measurement being generated by a photometer for light reflecting from a face of the eyeglass;

providing a value of UV reflection on a back face of the eyeglass, the UV reflection being obtained by integrating spectral reflection values relating to the back face of the eyeglass;

applying UV reflection of the eyeglass to a formula with a non-zero positive factor for the UV reflection; and calculating the index value from a non-zero base number divided by a result obtained in the applying step, the index value being based in part on measurements obtained from the obtaining a measurement step.

2. The method according to claim 1, wherein
the spectral reflection values are weighted for quantifying the hazard and intensity for each wavelength value over a determined UV wavelength range.

3. The method according to claim 2, wherein the determined UV wavelength range used in the step of providing the value of UV reflection is selected from a group of ranges including a first range from 280 nm to 380 nm, a second range from 280 nm to 400 nm, a third range from 315 nm to 380 nm, and a fourth range from 280 nm to 315 nm.

4. The method according to claim 2 further comprising:
providing a value of UV transmission for the eyeglass, obtained by integrating spectral transmission values weighted for quantifying hazard and intensity for each wavelength value, over the determined UV wavelength range.

5. The method according to claim 4, further comprising:
combining both values of UV transmission and UV reflection of the eyeglass using the formula with non-zero positive factors respectively for both the UV transmission and the UV reflection; and calculating the index value from a non-zero base number divided by a result obtained in the combining.

6. The method according to claim 5, wherein the index value calculated in the calculating step is equal to the base number divided by the result obtained in the combining step for the combining of the UV transmission and UV reflection values of the eyeglass using the addition formula.

7. The method according to claim 5, wherein quantifying the intensity for each wavelength value in the step of providing the value of UV transmission and the step of providing the value of UV reflection includes using values of solar spectral irradiance as a factor within a weighting function for the spectral transmission and spectral reflection values of the eyeglass.

8. The method according to claim 5, wherein the UV transmission is provided in the step of providing the value of UV transmission for a first value of an incidence angle of UV rays onto the eyeglass less than 30°, and the UV reflection is provided in the providing the value of UV transmission for a second value of incidence angle of UV rays onto the back face of the eyeglass between 135° and 160°, the incidence angles being measured from a forward-oriented reference direction of the eyeglass.

9. The method according to claim 5, wherein a ratio of the factor for the UV transmission of the eyeglass used in the combining step to the base number is in a range of from 0.01 to 1.

10. The method according to claim 5, wherein the addition formula used in the combining step is $\alpha\cdot R_{UV}+\beta\cdot\tau_{UV}+\gamma$, wherein:

$\tau_{UV}$ and $R_{UV}$ are, respectively, the values of the UV transmission and the UV reflection of the eyeglass, $\alpha$ and $\beta$ are the factors respectively for the UV reflection and the UV transmission of the eyeglass, and $\gamma$ is a constant value.

11. The method according to claim 10, wherein the factors of the UV reflection and the UV transmission values of the eyeglass in the addition formula are both equal to one, and the constant value is zero.

12. The method according to claim 2, further comprising:
generating the rating for the eyeglass with respect to the protection provided by the eyeglass against UV hazard based on the calculated index value; and
providing to a customer the rating for the eyeglass.

13. The method according to claim 1, wherein a ratio of the factor for the UV reflection on the back face of the eyeglass used in the applying step to the base number is in a range of from 0.01 to 1.

14. The method according to claim 1, wherein the factor for the UV reflection is used in the applying step for the eyeglass and is obtained from photometric measurements of the measuring step performed for direct solar UV intensity impinging onto the back face of the eyeglass from a back side of a wearer's head, with reference values for one or more parameters including illumination parameters in day time, sizing, wearing parameters of a spectacle frame used with the eyeglass, and a base parameter of the eyeglass.

15. The method according to claim 14, wherein the factor for the UV reflection used in the applying step for the eyeglass is obtained from averaged measurement results performed with varying one or more of the illumination parameters including a solar time, an azimuth direction of the wearer's head, an inclination of the wearer's head, a season, a date within a year, and a latitude on the Earth.

16. The method according to claim 1, wherein a result of the formula is obtained directly from measurements performed during the measuring step with the eyeglass using a bench photometer configured to simulate outside illumination conditions in day time.

17. A method of sorting a set of eyeglasses with respect to protection provided by each of the eyeglasses against UV hazard, comprising:
for each one of the eyeglasses, calculating a respective index value by implementing a rating method according to claim 1; and
comparing with each other the index values obtained respectively for the eyeglasses.

* * * * *